(12) United States Patent
Wild

(10) Patent No.: US 8,795,302 B2
(45) Date of Patent: Aug. 5, 2014

(54) SURGICAL CLIP

(75) Inventor: Andrew Michael Wild, London (GB)

(73) Assignee: Teresa Kathleen Wild, Jeddah (SA)

( * ) Notice: Subject to any disclaimer, the term of this patent is extended or adjusted under 35 U.S.C. 154(b) by 307 days.

(21) Appl. No.: 10/549,375

(22) PCT Filed: Mar. 12, 2004

(86) PCT No.: PCT/GB2004/001060
§ 371 (c)(1),
(2), (4) Date: Jan. 26, 2007

(87) PCT Pub. No.: WO2004/080314
PCT Pub. Date: Sep. 23, 2004

(65) Prior Publication Data
US 2007/0162060 A1    Jul. 12, 2007

(30) Foreign Application Priority Data

Mar. 14, 2003   (GB) .................................. 0305976.3

(51) Int. Cl.
*A61B 17/08*        (2006.01)

(52) U.S. Cl.
USPC ............................ 606/157; 606/151; 606/158

(58) Field of Classification Search
USPC ............... 606/157, 158, 151; 24/129 W, 130, 24/115 A; 251/9, 10; D28/39–43
See application file for complete search history.

(56) References Cited

U.S. PATENT DOCUMENTS

| | | |
|---|---|---|
| 3,120,230 A | 2/1964 | Skold |
| 3,535,746 A | 10/1970 | Thomas, Jr. |
| 3,616,497 A * | 11/1971 | Esposito, Jr. ................... 24/542 |
| 3,675,688 A | 7/1972 | Bryan et al. |
| 3,735,762 A | 5/1973 | Bryan et al. |

(Continued)

FOREIGN PATENT DOCUMENTS

| | | |
|---|---|---|
| CN | 2340384 Y | 7/1999 |
| DE | 4215449 C1 | 9/1993 |

(Continued)

OTHER PUBLICATIONS

Fox; Vascular clips for the microsurgical treatment of stroke; Stroke: Journal of the American Heart Association; Sep.-Oct. 1976; pp. 488-500; vol. 7, No. 5; downloaded on Jul. 9, 2010, from http://stroke.ahajournals.org/cgi/reprint/7/5/489.pdf.

(Continued)

*Primary Examiner* — Dianne Dornbusch
(74) *Attorney, Agent, or Firm* — Jason A. Bernstein; Barnes & Thornburg LLP

(57) ABSTRACT

A surgical clip for occluding a vein, artery or other body passageway 2 comprises a base portion 3, a pair of resilient limbs 4a, 4b configured to extend generally laterally outwardly from the base portion and each having a free end disposed forward of the base portion, and a reaction portion 9a/b mounted to the base portion 3, the reaction portion defining a generally forwardly directed reaction surface 10 disposed between the base portion 3 and the free ends of the limbs 4a, 4b, the limbs (4a, 4b) being movable under a resilient restoring force from a first, open, condition, in which a gap is provided between the limbs and the reaction portion for receiving the body passageway into the clip, to a second, closed, condition, in which the limbs cooperate with the reaction portion to grip the body passageway to occlude the same.

16 Claims, 5 Drawing Sheets

(56) References Cited

U.S. PATENT DOCUMENTS

| | | | |
|---|---|---|---|
| 3,807,675 A * | 4/1974 | Seckerson et al. | 248/73 |
| 4,449,530 A | 5/1984 | Bendel et al. | |
| 4,485,816 A | 12/1984 | Krumme | |
| 4,686,983 A | 8/1987 | Leisman et al. | |
| 4,878,276 A * | 11/1989 | Morrish et al. | 24/511 |
| 4,936,447 A | 6/1990 | Peiffer | |
| 4,950,258 A | 8/1990 | Kawai et al. | |
| 4,969,890 A | 11/1990 | Sugita et al. | |
| 4,976,722 A | 12/1990 | Failla | |
| 5,026,379 A | 6/1991 | Yoon | |
| 5,083,741 A * | 1/1992 | Sancoff | 251/9 |
| 5,171,252 A | 12/1992 | Friedland | |
| 5,192,288 A | 3/1993 | Thompson et al. | |
| 5,217,030 A | 6/1993 | Yoon | |
| 5,217,472 A | 6/1993 | Green et al. | |
| 5,217,473 A | 6/1993 | Yoon | |
| 5,219,353 A | 6/1993 | Garvey, III et al. | |
| 5,219,354 A | 6/1993 | Choudhury et al. | |
| 5,226,908 A | 7/1993 | Yoon | |
| 5,246,443 A | 9/1993 | Mai | |
| 5,259,366 A | 11/1993 | Reydel et al. | |
| 5,330,483 A | 7/1994 | Heaven et al. | |
| 5,356,064 A | 10/1994 | Green et al. | |
| 5,551,214 A | 9/1996 | Vincze et al. | |
| 5,564,262 A | 10/1996 | Bevis et al. | |
| 5,601,572 A | 2/1997 | Middleman et al. | |
| 5,618,311 A | 4/1997 | Gryskiewicz | |
| 5,733,329 A | 3/1998 | Wallace et al. | |
| 5,792,149 A | 8/1998 | Sherts et al. | |
| 6,138,678 A * | 10/2000 | Nilsson | 128/885 |
| 6,164,604 A * | 12/2000 | Cirino et al. | 248/74.3 |
| 6,443,958 B1 * | 9/2002 | Watson et al. | 606/120 |
| 6,607,542 B1 | 8/2003 | Wild | |
| 2002/0198535 A1 | 12/2002 | Watson, Jr. et al. | |

FOREIGN PATENT DOCUMENTS

| | | |
|---|---|---|
| EP | 0121362 A1 | 10/1984 |
| EP | 0 246 087 | 11/1987 |
| EP | 0386361 A1 | 9/1990 |
| EP | 0743045 A2 | 11/1996 |
| WO | 9213490 A1 | 8/1992 |
| WO | 9219144 A2 | 11/1992 |
| WO | 9616603 A1 | 6/1996 |
| WO | WO 97/28745 | 8/1997 |
| WO | 9740755 A1 | 11/1997 |
| WO | 9858591 A1 | 12/1998 |
| WO | 9962406 A2 | 12/1999 |
| WO | WO 00/35355 | 6/2000 |

OTHER PUBLICATIONS

Information Sheet for Ligaclip Titanium Ligating Clip from Ethicon, Inc.; downloaded on Jul. 9, 2010, from http://www.abcoremedical.com/.

Information Sheet for Ligaclip 20/20* Multiple Clip Applier from Ethicon, Inc.; downloaded on Jul. 9, 2010, from http://www.onlinemedicalresources.com/servlet/the-225/ethicon-ligaclip-appliers-small/Detail.

* cited by examiner

SURGICAL CLIP

PRIORITY CLAIM

This application is the national stage of International Application No. PCT/GB2004/001060, filed Mar. 12, 2004, which claims benefit to United Kingdom Patent Application No. GB0305976.3, filed Mar. 14, 2003, the specification of which is hereby incorporated herein by reference in its entirety.

FIELD OF THE INVENTION

The present invention relates to a surgical clip, particularly but not exclusively for use in haemostasis.

BACKGROUND OF THE INVENTION

An example of a commercially available haemostatic locking clip is the Hem-o-lok ligating clip, available from Weck Closure Systems, USA. This clip takes the form of a hinged plastic jaw with cooperating snap-fit closure formations on the end of each of the two jaw members. The clip is applied onto a blood vessel via a simple pliers-like applicator which closes the open jaw members together across the blood vessel, until the jaw members snap together. The clip has no inherent self closing bias, and the application mechanism is crude in that each clip must be loaded manually and individually on the applicator, in the open condition. To actuate the loaded applicator, a surgeon must make available his whole dominant hand, because of the pliers-grip hand action required.

A permanent occlusion cerebral aneurysm clip is on the market from Aesculap, under the name of the Yasargil-Phynox aneurysm clip. This clip takes the form of a spring-hinged cobalt-chrome (or sometimes titanium) metal alloy jaw provided with a self closing spring bias. The clip is applied onto a cerebral blood vessel via a simple pliers-like applier which initially opens the jaw members against the spring bias, so that the open jaw can be applied across the blood vessel. The applier can then be released, so that the jaw members spring together. Again, this clip suffers from the disadvantages that each clip must be loaded manually and individually on the applier, in the open condition, and, to actuate the loaded applier, a surgeon must make available his whole dominant hand, because of the pliers-grip hand action required.

WO-A-00/35355, the disclosure of which is incorporated herein by reference, describes a surgical apparatus and method for occluding or encircling a body passageway, e.g., for haemostasis. The method involves offering a surgical clip formed from a temperature-dependent shape-memory material, to a blood vessel or other body passageway in a first clip configuration at a temperature below body temperature, and allowing the temperature of the clip to rise by the proximity of the body passageway to the clip. The rise in temperature assists the clip to deform into a second, occluding, configuration in which the clip is closed around the body passageway.

One particular clip design is shown in FIGS. 19 to 21 of this prior art. The clip comprises an elongate element formed of circular cross-section shape-memory metal (Nitinol) wire shaped to have generally first and second ends and a sinuously curved intermediate central portion. The first and second ends of the wire element form legs of the clip and the sinuously curved intermediate central portion forms two apices directed towards the legs, which provide shoulders to which the closing force of the legs in the second configuration is directed. In effect, the legs of the clip squeeze the body passageway against the apices of the central portion of the clip to provide occlusion of the body passageway.

It is found that there is still room for improvement of the occlusive effect of the prior art clips.

BRIEF DESCRIPTION OF THE INVENTION

The present invention is based on my finding that the occlusive effect of the legs of such a clip on the body passageway is significantly improved if a reaction surface is provided as a feature of the clip.

Accordingly to the present invention, there is provided a surgical clip for occluding a body passageway, the clip comprising:
  a base portion,
  at least one resilient limb extending from the base portion and having a free end disposed forward of the base portion, and
  a reaction portion mounted to the base portion, the reaction portion defining a generally forwardly directed reaction surface disposed between the base portion and the free end of the limb or limbs,
the limb or limbs being movable under a resilient restoring force from a first, open, condition, in which a gap is provided between the limb or limbs and the reaction portion for receiving the body passageway into the clip, to a second, closed, condition, in which the limb or limbs cooperate with the reaction portion to grip the body passageway to occlude the same.

Exemplified Features of the Clip

Preferably, the limb or limbs of the clip extend generally laterally outwardly from the base portion of the clip. Most preferably, the clip has a pair of such limbs each extending in opposite lateral directions from the base portion of the clip. The base and reaction portions are preferably disposed generally centrally between the pair of limbs.

The reaction surface is preferably substantially fixed in relation to the movement of the limb or limbs. The reaction surface is preferably elongate. The reaction surface may be straight or curved, and preferably has the form of a ridge or edge. The reaction surface and the limb or limbs are suitably dimensioned and arranged so that in the closed condition of the clip substantially the entire transverse width of the occluded body passageway is in contact with the reaction surface.

The clip is preferably generally planar, but the respective planes of the parts may be offset against one another. Thus, for example, the plane of the reaction portion may be at a small angle (e.g. up to about 15°) to the plane of the base portion, with a slight twist provided at the region of connection between the two portions. The plane of the or each limb may be at a small angle (e.g. up to about 15°) to that of the base portion. Where the clip has a pair of limbs, it is preferred that one limb lies slightly to one side of the plane of the base portion, and the other limb lies slightly to the opposite side of that plane. The free ends of the limbs thereby overlie each side of the reaction portion—itself preferably lying in a plane which is slightly offset relative to the plane of the base portion—in the closed condition of the clip. The direction and angular extent of the offsetting of the plane of the reaction portion are preferably such that the free end of a limb approaches close to the reaction surface in the closed condition of the clip, enhancing the grip on an intervening body passageway in comparison with a clip in which the reaction portion would not have been offset from the plane of the base portion. In this way, a particularly efficient and secure occlusive effect can be achieved, with less bending of the limb(s) out of the plane than would have been necessary to achieve the same occluding effect if the plane of the reaction portion were not offset in relation to the base portion.

The reaction surface may be shaped in a manner generally complementary to the shape of those parts of the limb or limbs which cooperate with the reaction surface in the second condition of the clip. At least one of the opposed cooperating parts of the reaction surface and the limb or limbs may suitably be provided with surface projections which serve in use to enhance the grip on the body passageway. Such projections may include rounded teeth, pointed teeth, nipping heads, or any combination thereof. Teeth or nipping heads may be turned in the manner of a shark's fin, if desired.

At least one of the reaction surface and the limb or limbs may suitably be provided with one or more guide projections which serve during closure of the clip to guide the body passageway to lie in a particular—preferably central—region of the clip. The guide projections may conveniently have a rounded shape.

The reaction portion of the clip is preferably connected to the base portion via a relatively narrow neck.

It is preferred that the or each limb extends from the base portion of the clip behind the reaction portion of the clip and initially turns backwards, i.e., away from the forward facing direction of the reaction surface, and that the or each limb has at least one further turn ("elbow") in its length, after which it extends in the forwards direction to cause the free end of the limb to extend forwardly of the reaction surface. The turns may suitably be smooth curves. Such a configuration has the advantage that the stress applied to open the limbs against the resilient restoring (closing) force of the limbs is spread over a relatively long limb length, so reducing the risk of failure or loss of resilience. Furthermore, by providing for a relatively long limb length, useful leverage or mechanical advantage can be obtained in the closing of the limb towards the reaction surface. The majority of clip closure takes place at the elbow section of the limb. However, when the clip closes around a body passageway there is some straightening of the other turns, as additional length is transferred from such other sections into the gripping part of the limb, so providing the leverage referred to above.

The base portion of the clip is suitably in the form of an open loop or generally U shaped member having a closed end directed away from the limb or limbs and an open end from which the limb or limbs and the reaction portion extend. As viewed from above the general plane of the clip, the clip has a left hand side and a right hand side. These sides may preferably be generally symmetrical about a central axis of symmetry. The open ends of the loop preferably lie close to either side of said axis in both the open and the closed conditions of the clip. The reaction portion of the clip may be connected to the base portion via a single neck region at one of said left and right sides of the loop of the base portion, or alternatively the reaction portion of the clip may be provided in two halves, each of which is connected to one side of the base portion via a neck region. The two halves may be complementarily juxtaposed to provide the reaction surface of the clip.

The base portion of the clip is preferably provided with a weak region or point at which it may be cut after use in such a way that the clip, in its second, closed, condition, can be removed from the body passageway. The weak region or point may preferably be provided with a notch or mark to assist the procedure.

The parts of the clip are preferably integral with each other and the clip is preferably formed in one piece from a sheet of a resilient material. The sheet will preferably have a uniform thickness in the range of about 500 to about 1000 μm, depending on the size of clip required. Suitable resilient materials include shape-memory materials whether of the temperature-induced or stress-induced type. Suitable materials are identified in WO-A-00/35355. A useful class of materials is that described generally as superelastic or stress-induced shape-memory materials. Such materials are well known in the art generally. A preferred material is Nitinol metal (nickel-titanium alloy), more preferably Nitinol having an Active Austenite Finish (Active $A_f$) temperature of around 15° C. within normal Nitinol tolerance.

Manufacture of the Clip

The clip may suitably be manufactured by photochemical etching or laser cutting from a sheet of the resilient material. A suitable sheet material will be a flat, annealed, surface pickled, Nitinol sheet of 800 μm thickness, available from SMA, Inc. of San Jose, USA under Alloy Code S (approx. 55.8 wt % nickel; balance titanium). Such a sheet has an Active $A_f$ temperature of around 15° C. within normal Nitinol tolerance. Laser cutting is preferred. The use of an industrial laser has been found to be advantageous, in that no extraneous metals are added to the surface composition of the clip by this process. The laser cutting technique provides the required degree of accuracy and does not adversely affect the superelasticity of the Nitinol.

The clip is preferably obtained initially as a planar blank with the limb(s) arranged in an intermediate condition, i.e., with the limb(s) neither fully opened, nor too closed to interfere with reaction portion. The intermediate condition should be sufficiently close to the first (open) condition that the first condition of the clip can be obtained by stressing the limb(s) outwardly by less than the maximum recoverable strain of the resilient material used. In the case of Nitinol, its maximum recoverable strain is 6 to 8%, which means in practice that the limb(s) of the blank as cut should lie sufficiently close to its/their orientation in the first condition of the clip that the first condition can be achieved by moving the limb(s) outwardly by an angular deformation of less than about 8°.

Following this, a batch of formed clips will preferably be sandblasted to remove burrs from the cut edges. After this, they undergo a two stage shape setting process (shape set annealing twice).

In stage one, the reaction portion of the clip is rotated slightly out of the plane of the blank, sufficient to allow the limb(s) to move easily into the closed condition. The clip is then shape set annealed to permanently set this alteration.

In stage two, the or each limb is turned inwards into the closed condition, e.g., using a jig. In addition, the or each limb is slightly off-set above or below the plane of the blank, to pass in front of, or behind, the reaction portion. The formed clip is then constrained and heat treated to permanently set the closed shape (shape set annealed).

Lastly, the clips are suitably electropolished to round off the edges and the surface passivated by means of a biocompatible oxide or organic coating. Such a coating may suitably comprise titanium dioxide, parylene, or any other conventional biocompatable material.

Before opening the clip, cooling needs to be applied to below the Active $A_f$ temperature of the Nitinol. This technique is used to recover the intermediate condition prior to loading a plurality of clips into the applicator (see below). The clip will then show good superelasticity in response to a stress in a temperature window above the Active $A_f$ temperature and below body temperature. Under these conditions, the clip will move strongly to its second, closed condition.

Use of the Clip

The clip is primarily used to occlude a body passageway during surgery. The term "occlude" refers to an encircling and constricting action, rather than a piercing or cutting action. In some cases, the occlusive effect of the clip should be reversible.

The preferred embodiment of the clip of the present invention may be used either for reversible or for irreversible procedures, giving the patient a choice in appropriate cases between reversal and permanence.

The clip is preferably applied to the body passageway to be occluded using an applicator apparatus corresponding generally to the apparatus described in WO-A-00/353855. A plurality of clips is held in a train in the apparatus with the limb(s) in an unstressed, intermediate, condition. In this unstressed condition, a substantial superelastic response tending to close the clip will not take place. In response to actuation of the applicator mechanism by the surgeon, one clip is stressed in the apparatus by being moved over a suitably shaped surface so that the limb(s) is/are deflected outwardly by an amount within the maximum recoverable stress of the material of the clip. The clip is then dispensed, limb(s) first, from a port of the apparatus, whereupon the limb(s) immediately close(s) around the body passageway and occlude(s) the same, preferably without cutting, puncturing or penetrating the body passageway or any adjacent structures. The port of the apparatus will be such that the clip is not fully released until the clip is well located. Depending on the material from which the clip is manufactured, it may not be necessary for any change in temperature to take place in order to induce the closure of the limb(s) into the second condition of the clip. The stressing immediately prior to dispensing of the clip from the apparatus will in many cases be sufficient to induce the resilient transformation of the clip.

Alternatively, large clips may be applied manually to a body passageway, suitably with the aid of a trocar or other simple stressing device to slightly splay the limbs to activate the superelastic closing force.

Where not otherwise stated herein, the details of the clip of the present invention will correspond generally to the clips defined and described in WO-A-00/35355 where the context permits.

By providing a clip which has a reaction surface as described, the efficacy of the occluding and clamping action of the clip on a body passageway is markedly improved, particularly in the case of small arteries and veins that may otherwise be difficult to close effectively. Furthermore, the clip of the present invention can be readily manufactured in large numbers from a sheet of the resilient material.

The clip will be dimensioned according to the desired use. Typical uses of the clip will include the surgical closure of veins and arteries for haemostasis; ligation; male and female sterilisation; vascular occlusion; cardiac vessel occlusion; the occlusion of body ducts prior to resection; intracranial vessel occlusion for neurosurgery; occlusion of aberrant vessels or aneurysms such as intracranial aneurysm clipping; and occlusion of arterio-venous malformations. In each case, the clip can be dimensioned to be suitable for paediatric, adult or veterinary surgery.

A clip size of about 6 mm width will generally be suitable for occluding body passageways having a diameter in the range of about 3 to about 5 mm. Corresponding size adjustments can readily be made to cater for different sizes of passageway.

The clips of the present invention may conveniently be supplied in standard sizes, to cater for body passageways within a defined diameter range. It is envisaged that clips may suitably be supplied in sizes suitable for 1-2 mm passageways, 2-3 mm passageways, 3-5 mm passageways, and so on.

BRIEF DESCRIPTION OF THE DRAWINGS

An embodiment of the present invention will now be described in further detail, purely by way of example and without limitation, with reference to the accompanying drawings.

In the drawings.

DETAILED DESCRIPTION

Figure 1:
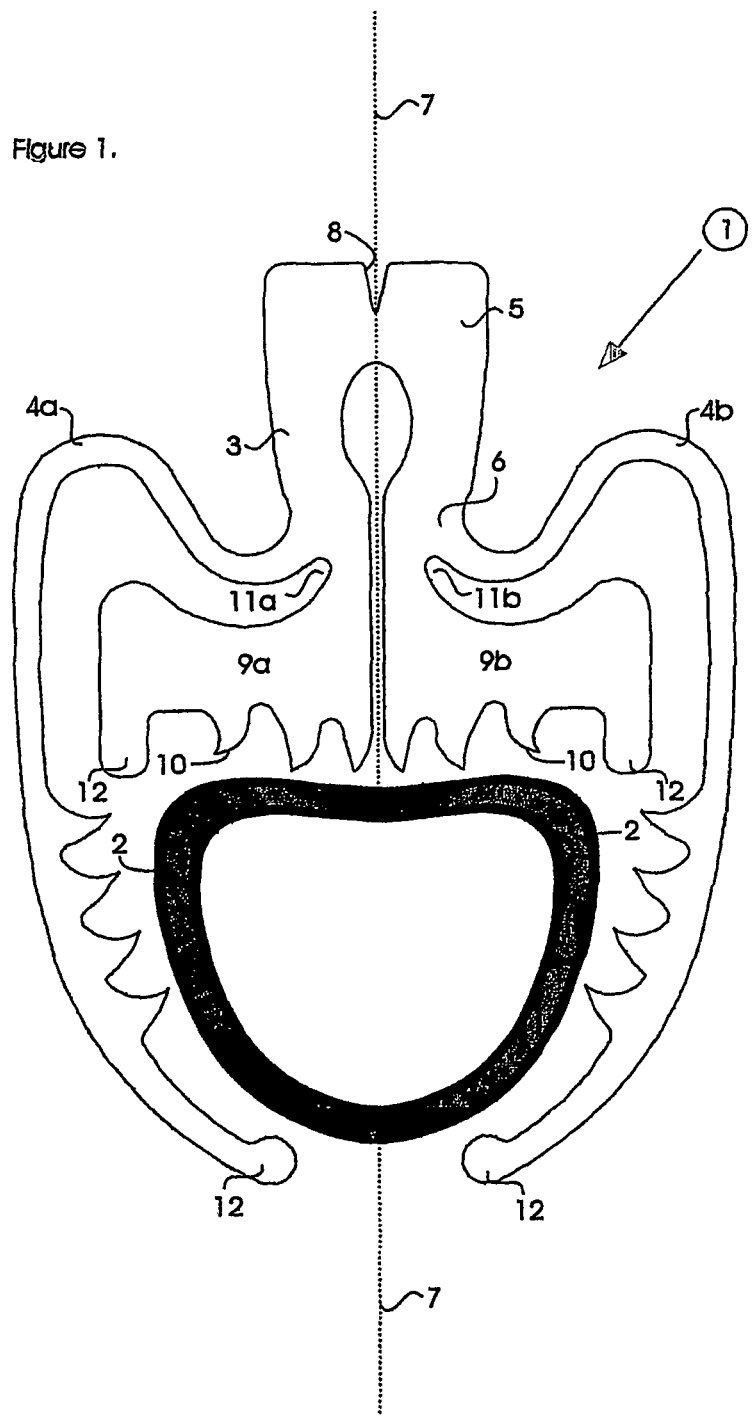
FIG. 1 shows a surgical clip in the first condition applied to a body passageway, looking along the line of the body passageway.

Referring to the drawings, there is shown a surgical clip 1 for occluding a body passageway 2, e.g., for haemostasis.

The clip 1 comprises a base portion 3 and a pair of resilient limbs 4a, 4b extending laterally outwardly from the base portion. The limbs 4a, 4b are resiliently movable from a first, open, condition (FIG. 1; FIG. 2, solid lines), in which the limbs are spaced apart to define a gap for receiving the body passageway 2, to a second, closed condition (FIGS. 3 to 5), in which the limbs 4a, 4b are closed around the body passageway to occlude it. The occlusion of the body passageway is a simple closing (pinching), without puncture or rupture, and can be reversed by removing the clip, as will be described in more detail below.

The base portion 3 of the clip is in the form of an open U-shaped loop having a closed end 5 directed away from the limbs 4a, 4b and open end 6 at which the limbs 4a, 4b are connected.

Figure 2:
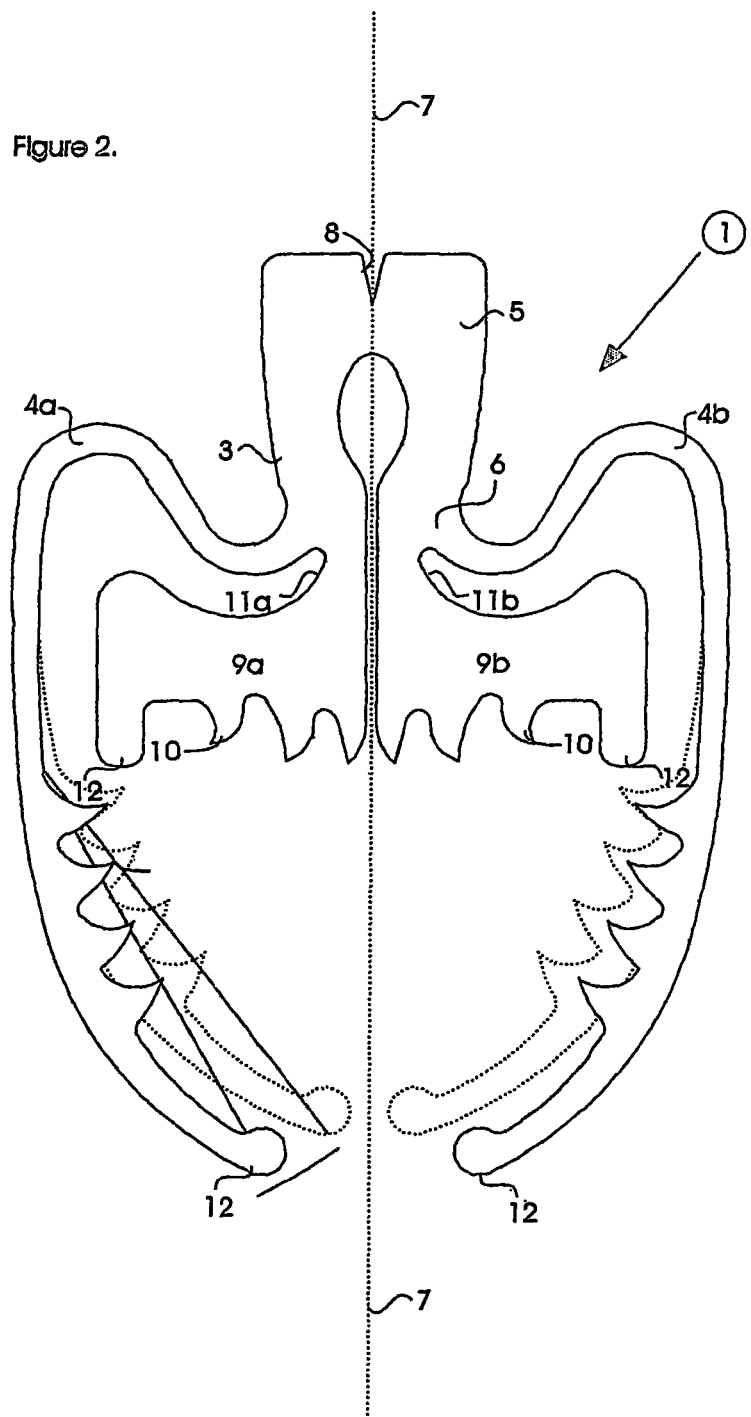
FIG. 2 shows the surgical clip of FIG. 1 omitting the body passageway for clarity, and in dotted lines the resting or intermediate condition of the clip prior to stressing to achieve the first condition.
Figure 3:
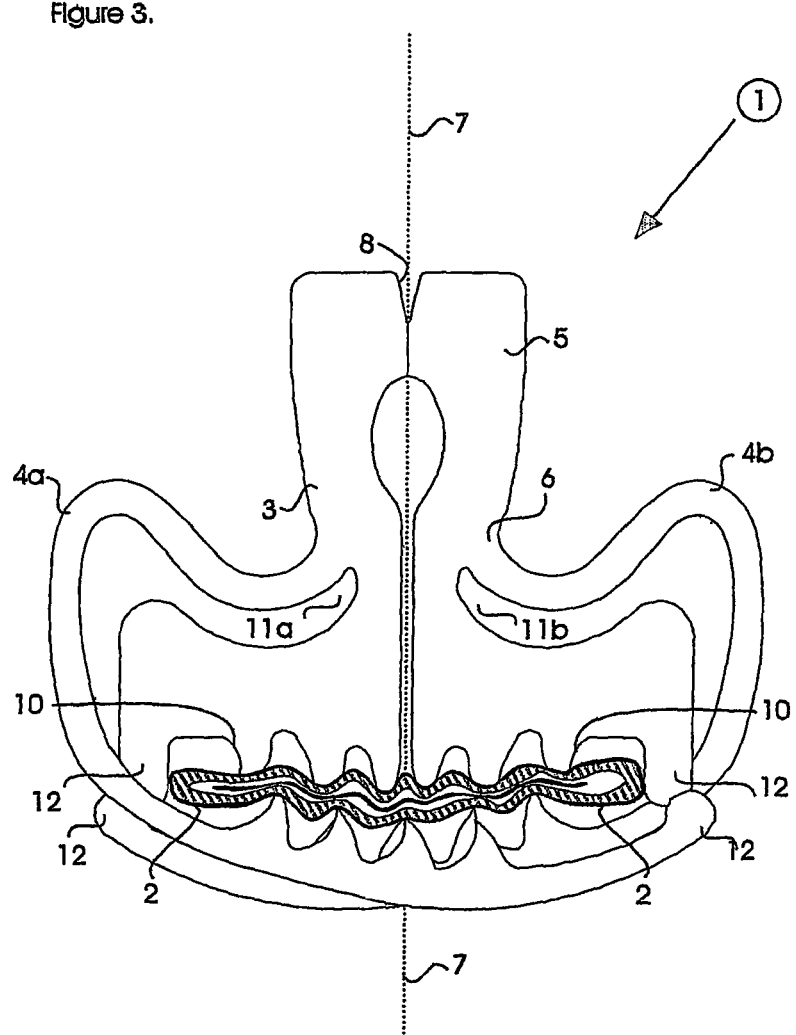
FIG. 3 shows the surgical clip and body passageway in the closed condition (occluded body passageway)

As shown particularly in FIGS. 1 and 2, the clip consists of symmetrical left and right parts, the clip having a central axis of symmetry or midline 7. The closed end 5 of the loop is provided with a notch 8 defining a point at which the central body portion 3 of the clip can be cut. Such cutting will release the clip from its closed condition on the body passageway (FIGS. 3 to 5), to enable removal of the clip from the body passageway.

The clip 1 includes, in separate but complementarily juxtaposed left and right parts 9a, 9b with respect to the central axis of symmetry 7 of the clip, a reaction portion which projects from the base portion and defines, at a location forward of the base portion but behind the free ends of the limbs 4a, 4b an elongate forwardly directed reaction surface 10 arranged cooperate with the limbs 4a, 4b in the second (closed) condition of the clip so that substantially the entire transverse width of the occluded body passageway 2 is in contact with the reaction surface 10 for being gripped between the limbs 4a, 4b and the reaction surface. The reaction surface 10 is in the general form of an edge which serves to pinch the body passageway 2 without severing it.

Each of the left and right parts 9a,9b of the reaction portion is connected to the respective left or right side of the central body portion 3 of the clip via relatively thin neck 11a, 11b.

The reaction surface 10 and the limbs 4a, 4b are provided with rounded guide projections 12 which serve in use to guide the body passageway 2 to lie in a generally central region of clip 1.

Figure 4:
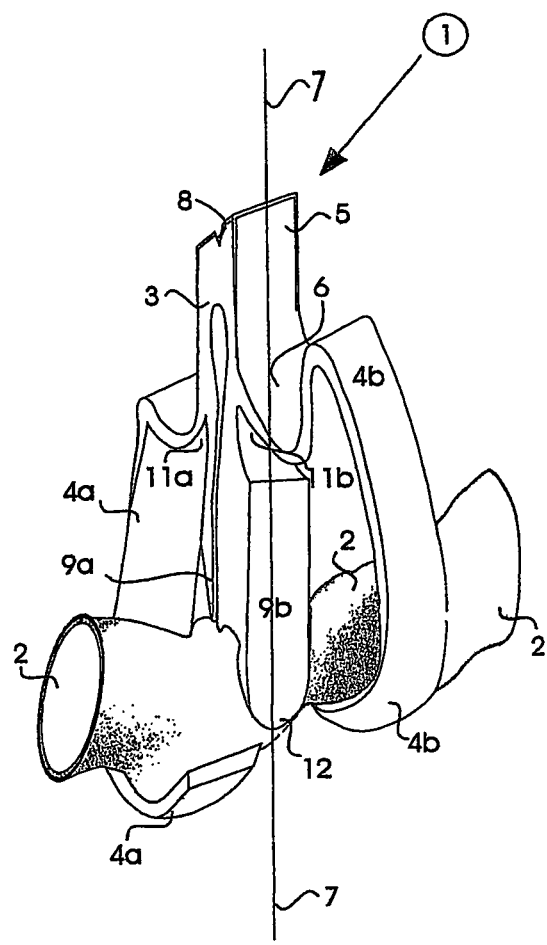
FIG. 4 shows in perspective the surgical clip and body passageway of FIG. 1 from front right.

As shown particularly in FIG. 4, one limb 4a lies to one side of the edge of the reaction surface 10, i.e., slightly to the left of the vertical plane of the central body portion 3 of the clip as viewed, and the other limb 4b lies to the other side of the edge of the reaction surface 10, i.e., slightly to the right of the plane of the central body portion 3 of the clip as viewed. In addition, the central reaction portion 9a, 9b is rotated (off-set) anti-clockwise from the neutral, planar, laser cut condition, to further facilitate movement of each of the limbs 4a, 4b to pass unhindered to its respective side of the reaction surface 10.

The closure of the limbs 4a,4b is achieved by a straightening of some curves of the limbs and a tightening of others. The other portions of the clip are configured so that they do not foul the movement of the limbs. As previously explained, the shape of the limbs has been found to provide a useful leverage effect, maximising the occlusive effect within the capabilities of the shape-memory material being used. The location of the reaction surface between the limbs and forward of the central body portion of the clip provides further advantages in that the occlusive effect can be achieved to the desired extent without excessive tightening of any curve of the limbs being required.

Figure 5:
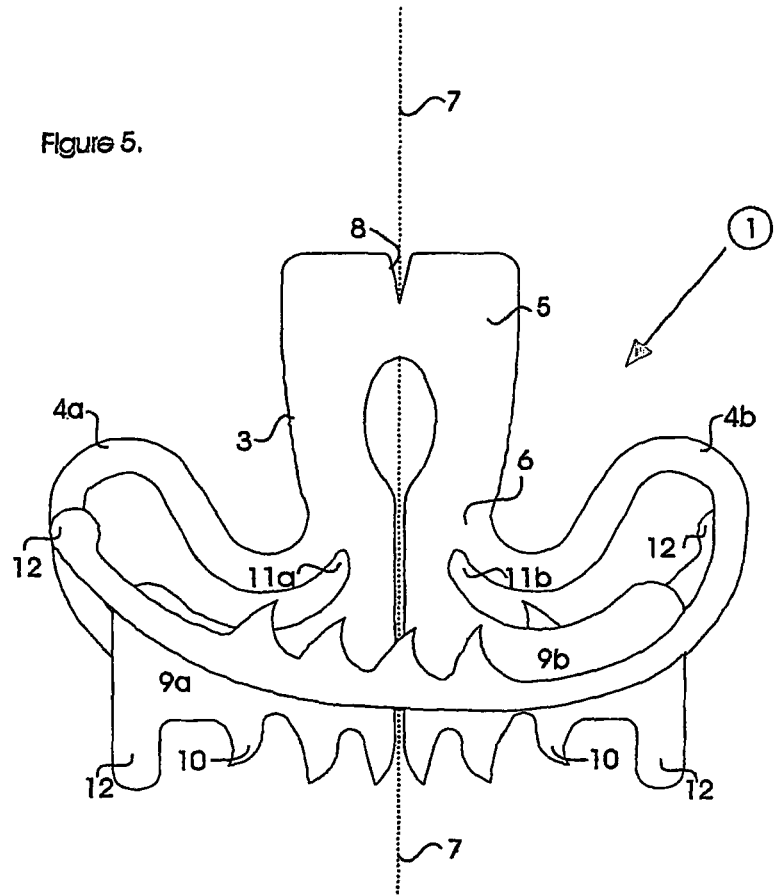
FIG. 5 shows the surgical clip in a fully closed condition achievable without a body passageway.

The clip 1 is formed by laser cutting a suitable "blank" shape from a sheet of Nitinol alloy having an Active $A_f$ temperature of about 15° C. The thickness of the sheet will be chosen according to the desired dimensions, end use and closing force of the clip. I have found, for example, that a sheet thickness of between about 500 and 1000 μm (e.g. about 800 μm) is suitable for forming a clip for occluding veins and arteries. The initially cut blank shape is planar and has the shape shown by the dotted lines in FIG. 2. The closed condition of the limbs as shown in FIG. 5 is then memorised into the clip in the manner described above. The initial orientation of the limbs is selected so that they are capable of being deflected slightly outwards (e.g. by an angle up to about 8°), within the limit of deformation, to stress the limbs and induce a superelastic or pseudoelastic response, urging the limbs to close when the stress is released. If the clip is not applied to a body passageway, the fully closed condition shown in FIG. 5 will result, in which the limbs 4a and 4b lie across the off-set central reactive portion 9a and 9b. If, on the other hand, the clip is applied to a body passageway as described above, it will close to the condition shown in FIGS. 3 and 4 when the stress is released.

After memorising of the shape, the clips are electropolished to round off the edges and a passive, closed layer of titanium dioxide is created (surface passivation), which is more biocompatible than the metal. The electropolishing process reduces the clip thickness to about 730-750 μm. The active $A_f$ of the finished product is around 15° C., which means that the clips are superelastic, but also exhibit shape memory function (Austenite closed shape preference) at temperatures above 15° C. Chemical analysis confirms that the final composition of the clip contains 50.91 at % nickel and that the nickel content at the surface, following surface passivation, is <5 at %. The deposited surface layer of titanium dioxide is approximately 50-80 nm thick, which has been found to produce good biocompatibility.

The foregoing broadly describes the invention without limitation to particular embodiments thereof. Variations and modifications as will be readily apparent to those of ordinary skill in this art are intended to be included within the scope of this application and subsequent patent(s).

The invention claimed is:

1. A surgical clip for occluding a compressible tube-like body passageway having a longitudinal axis, the surgical clip comprising:
   a) a generally planar base portion having
      i) a first face in a first face plane,
      ii) a second face in a second face plane, the first and second face planes being parallel to each other, the first face facing in a first facing direction orthogonal to the first face plane and the second face facing in a second facing direction orthogonal to the second face plane and opposed to the first facing direction,
      iii) a first axis lying in the first face plane defining a midline of the first face plane, and
      iv) a second axis lying in the second face plane defining a midline of the second face plane, the first and second axes being parallel to each other and both lying in a central plane transecting the planar base portion orthogonal to the first and second face planes, the central plane defining a boundary between opposite first and second lateral regions of the clip, a direction along the parallel first and second axes constituting a forward direction of approach of the clip in an open condition towards the body passageway for engaging the body passageway prior to occlusion thereof;
   b) a first resilient arm having
      i) a proximal portion which is connected to the planar base portion and extends therefrom in the first lateral region of the clip,
      ii) a distal end portion defining an elongate first contact surface for contacting the body passageway at a first location on the longitudinal axis of the body passageway in a closed condition of the clip, and
      iii) a portion intermediate the proximal and distal end portions, which in the open condition of the clip is configured to cause the distal end portion of the first resilient arm to project in generally the forward direction of approach and angled in the first facing direction away from the first face plane;
   c) a second resilient arm having
      i) a proximal portion connected to the planar base portion and extending therefrom in the second lateral region of the clip,
      ii) a curved distal end portion defining an elongate second contact surface for contacting the body passageway at a second location, distinct from the first location, on the longitudinal axis of the body passageway in the closed condition of the clip, and
      iii) a portion intermediate the proximal and distal end portions, which in the open condition of the clip is configured to cause the distal end portion of the second resilient arm to project in generally the forward direction of approach and angled in the second facing direction away from the second face plane,
   a portion of the planar base portion and the first and second resilient arms being adapted to define, in the open condition of the clip, a gap in which the body passageway can be received with its longitudinal axis lying in the central plane parallel to the first and second directions when the clip engages the body passageway in the forward direction of approach; and
   d) a reaction portion having
      i) a neck region which extends from the base portion in a direction which is the same as the forward direction of approach and connects the reaction portion to the planar base portion so that the reaction portion is located forward of the planar base portion in the direction, and ii) an elongate third contact surface facing in the forward direction for contacting the body passageway at a third location on the longitudinal axis of the body passageway, the third location being distinct from and between the first and second locations, wherein the first and second resilient arms are adapted to move, under a resilient restoring force, from the open condition to the closed condition of the clip in which the third contact surface bears against the body passageway in generally the direction of approach and the first and second contact surfaces bear against the body passageway in generally the opposite direction to the direction of approach, the distal end portion of the first resilient arm being angled in the first direction away from the first face plane and the distal end portion of the second resilient arm being angled in the second direction away from the second face plane;

whereby the clip is capable of gripping the body passageway by the first, second and third contact surfaces of the clip at three distinct locations on the longitudinal axis of the body passageway, the third location being distinct from and between the first and second locations.

2. The surgical clip according to claim 1, wherein the reaction surface is substantially fixed in relation to the movement of the first and second resilient arms.

3. The surgical clip according to claim 1, wherein the elongated third contact surface is shaped in a manner generally complementary to the shape of those parts of each first and second resilient arm which cooperate with the elongated third contact surface in the closed condition of the clip.

4. The surgical clip according to claim 1, wherein at least one of the elongated third contact surface and the first and second resilient arms have surface projections which enhance the grip of the clip on the body passageway when engaged.

5. The surgical clip according to claim 4, wherein the surface projections are of a type selected from the group consisting of rounded teeth, pointed teeth, nipping heads, and any combination thereof.

6. The surgical clip according to claim 1, wherein each first and second resilient arms is connected to the planar base portion of the clip via a curved portion of the first and second resilient arms defining a connection point to the planar base portion behind the reaction portion of the clip.

7. The surgical clip according to claim 6, wherein a further curve is provided in the first and second resilient arms in the opposite direction to the said curved portion, whereby the free end of the first and second resilient arms is disposed forward of the planar base portion of the clip.

8. The surgical clip according to claim 7, wherein an elongate portion is provided in each first and second resilient arms between the curves, whereby during closure a leverage effect is produced on the part of the first and second resilient arms which is in contact with the body passageway.

9. The surgical clip according to claim 6, wherein the proximal portion of each of the first and second resilient arms includes an elongated curved section adapted to produce a leveraging effect when the first and second resilient arms are moved during closure to engage the body passageway.

10. The surgical clip according to claim 1, wherein the planar base portion of the clip is in the form of an open loop or generally U-shaped member having a closed end directed away from the first and second resilient arms and an open end at which the limbs and the reaction portion are connected to the planar base portion.

11. The surgical clip according to claim 10, wherein the reaction portion of the clip includes a first and second section, each section being connected to one side of the open end of the planar base portion via the neck region, the first and second sections being complementarily juxtaposed and which together define the third contact surface of the clip.

12. The surgical clip according to claim 1, wherein the planar base portion of the clip further comprises a separable region at which the planar base portion may be separated to remove the clip from the body passageway.

13. The surgical clip according to claim 1, wherein the clip is made of a superelastic or pseudoelastic shape-memory material.

14. The surgical clip according to claim 1, wherein the clip is made of sheet nitinol metal (nickel-titanium alloy).

15. The surgical clip according to claim 1, wherein the third contact surface and the first and second resilient arms are suitably dimensioned and arranged so that in the closed condition of the clip, substantially an entire transverse width of the occluded body passageway is in contact with the third contact surface.

16. The clip of claim 1, wherein said first face plane of said planar base portion is angled with respect to a plane defined by said elongated third contact surface.

* * * * *